United States Patent [19]

Kersten et al.

[11] Patent Number: 5,563,345
[45] Date of Patent: Oct. 8, 1996

[54] DEVICE FOR ULTRASONIC IDENTIFICATION OF FINGERPRINTS

[75] Inventors: Ralf T. Kersten, Bremthal; Volker Oehmke; Guenter Thorwirth, both of Jena, all of Germany

[73] Assignee: Jenoptik GmbH, Jena, Germany

[21] Appl. No.: 362,420

[22] PCT Filed: Apr. 18, 1994

[86] PCT No.: PCT/EP94/01194

§ 371 Date: Dec. 29, 1994

§ 102(e) Date: Dec. 29, 1994

[87] PCT Pub. No.: WO94/24937

PCT Pub. Date: Nov. 10, 1994

[30] Foreign Application Priority Data

Apr. 30, 1993 [DE] Germany ............... 43 14 220.6
Nov. 6, 1993 [DE] Germany ............... 43 37 918.4

[51] Int. Cl.⁶ ................................................ G01N 29/00
[52] U.S. Cl. ........................... 73/602; 73/606; 73/628; 382/124
[58] Field of Search ..................... 73/602, 642, 644, 73/628, 606; 382/4, 5; 364/506

[56] References Cited

U.S. PATENT DOCUMENTS

| 4,086,818 | 5/1978 | Reynolds . | |
|---|---|---|---|
| 4,977,601 | 12/1990 | Bicz | 382/4 |
| 5,211,059 | 5/1993 | Hayakawa et al. | 73/606 |
| 5,218,644 | 6/1993 | Bauer | 382/4 |
| 5,224,174 | 6/1993 | Schneider et al. | 73/602 |
| 5,258,922 | 11/1993 | Grill | 382/4 |

FOREIGN PATENT DOCUMENTS

| 0451565 | 10/1991 | European Pat. Off. . |
| 2919181 | 11/1980 | Germany . |
| 4016105 | 12/1990 | Germany . |
| 2009407 | 6/1979 | United Kingdom . |

OTHER PUBLICATIONS

Sound and Ultrasound Waves in Air, Water and Solid Bodies, (V. A. Krasil'nikov) 1963, National Science Foundation, Jersualem, IL, Third Edition, Translated from Russian (pp. 194–196).

Fundamentals of Ultrasonics, ( J. Blitz, et al) 1967, Butterworths, London, GB Second Edition (pp. 37–38).

Primary Examiner—Hezron E. Williams
Assistant Examiner—Nashmiya Ashraf
Attorney, Agent, or Firm—McAulay Fisher Nissen Goldberg & Kiel, LLP

[57] ABSTRACT

A device for identifying fingerprints by use of ultrasound having an electronic evaluating circuit, a hollow cylinder of length L with a cover and a base plate, wherein the ultrasonic speed through the liquid equals c' and the cover is made from a material with ultrasonic speed c". The outer side of the cover is planar to serve as a supporting surface for the fingerprint. The inner side is either convex (c'>c') or concave (c'<c") with a spherical radius R and the condition $L=R/|(c''/c')-1|$ must be satisfied. The individual ultrasonic receiver is arranged in the center of the base plate and extends over the smallest possible surface area. At least one annular transmitter is arranged concentrically around the individual ultrasonic receiver.

7 Claims, 1 Drawing Sheet

DEVICE FOR ULTRASONIC IDENTIFICATION OF FINGERPRINTS

BACKGROUND OF THE INVENTION

1. Field of the Invention

The invention is directed to a device for identifying fingerprints by use of ultrasound having an electronic evaluating circuit, a body which is filled with liquid and has a supporting surface with a plane outer side for the fingerprint to be analyzed, an ultrasonic transmitter and ultrasonic receiver, and is used for identifying fingerprints as means for authorizing access for persons to technical systems, rooms, vehicles, etc.

The invention serves in particular to replace PIN numbers used in connection with banking cards or other authorization identification. Accordingly, the invention can be applied in such areas as

- use of automatic tellers and the like by means of banking cards
- monitoring access to rooms and buildings by means of authorization cards
- authorized use of computing devices, motor vehicles, etc.

2. Description of the Related Art

There are a number of known commercially available technical solutions which are based on graphical comparison of the skin surface of the finger with reference patterns stored in computer memory. For this purpose, the fingerprint to be analyzed is photographed by a pixel-oriented opto-electronic camera (e.g., a CCD matrix camera), the measured values are convened in an analog-to-digital converter or ADC and entered in an electronic computer in which they are compared with reference images, e.g., based on the patterns of the fingerprint, which are stored in the computer memory.

A process and an arrangement using ultrasonic waves for analyzing fingerprints instead of photo-optical (imaging) elements is known from DE-OS 36 10 397, wherein the following possibilities were considered:

- An ultrasonic hologram is generated and implemented in a card.
- Human skin is exposed to ultrasonic radiation to detect a fingerprint, the ultrasonic radiation in its entirety or in part, depending upon the concrete arrangement, is directed onto the hologram.
- The occurring interference patterns of the (coherent) ultrasonic waves can be used for identification, for example, by way of correlation analysis.

The application of ultrasonic waves as described above has the following advantages:

- the identification process is relatively stable in the face of environmental influences (e.g., small surface-area disfigurement or soiling of the examined skin region) due to the holistic character of feature detection;
- deep skin regions (epithelial layer) are also included in feature detection so that it is relatively forgery-proof;
- due to the physical properties of ultrasonic waves, the amount of wave amplitude as well as its phase can be utilized for feature detection so as to increase reliability of identification.

Further, it is obviously possible to realize devices on the basis of ultrasound which are smaller, more robust and less expensive than devices based on optical, graphical comparisons.

An arrangement in which a quantity of individual elements arranged in matrix form is provided as ultrasonic transmitter and/or ultrasonic receiver is described in DE-OS 40 16 105 "Process and Arrangement for Determining Surface Structures". The individual transmitter elements are preferably actuated successively in time in a pulsed manner. In this type of operation, the transmitter matrix and the receiver matrix can be identical and the individual elements are operated optionally as transmitters or receivers via a measuring point change-over switch. Further, it is obvious that the matrix form can be substituted by arranging pairs of transmitters and receivers on a scanner.

Based on the laws of Fourier transforms, it is obvious that the individual receiver signals in such an arrangement are not invariant with respect to rotation of the fingerprint on the supporting surface.

Moreover, since the received signals are (complex) sound amplitudes in analogous Fourier transforms with the use of ultrasound, the receiver signals also depend on the positioning of the fingerprint (multiplicative linear phase function corresponding to the displacement rule of Fourier transforms).

OBJECT AND SUMMARY OF THE INVENTION

The primary object of the present invention is to provide a device for identifying fingerprints by means of ultrasound according to the of the general nature described above so as to obtain receiver signals which are invariant with respect to rotation and translation relative to changes in position of the fingerprint on the supporting surface.

In accordance with the invention, in a device for identifying fingerprints by use of ultrasound having an electronic evaluating circuit, a body which is filled with liquid and has a supporting surface with a plane outer side for the fingerprint to be analyzed, and an ultrasonic transmitter and ultrasonic receiver, wherein the ultrasonic transmitter and the ultrasonic receiver are arranged opposite the supporting surface, the ultrasonic speed through the liquid equals c' and the ultrasonic speed through the supporting surface equals c", the object is met in that the body is constructed as a hollow cylinder with a length L and with a cover serving as supporting surface and with a base plate, in that the inner side of the cover is either convex, where c' is greater than c", or concave, where c' is less than c", with a spherical radius R and the following condition is met $$L = R/|(c''/c') - 1|,$$

in that the ultrasonic receiver is a punctiform individual receiver and is arranged in the center of the base plate, in that the ultrasonic transmitter is formed by at least one annular transmitter arranged concentrically around the individual receiver, and in that in order to eliminate the dependence of the receiver signal supplied by the individual receiver on the translational movement of the fingerprint on the supporting surface, the electronic evaluating circuit contains means for rectifying the alternating electric signal delivered by the individual receiver and also contains means for integrating for the duration of an ultrasonic wave train which is received for every ultrasonic pulse emitted by the ultrasonic transmitter. Accordingly, with the device according to the invention, a 1:1 imaging of the ultrasonic transmitter is effectively carried out via two plano-convex or plano-concave ultrasonic lenses arranged symmetrically in the beam path, the diffracted or bending fingerprint structure being located in their common aperture stop, wherein the total focal length is equal to L/2. Every annular transmitter can be so designed that it can be actuated as a whole and as individual annular segments.

The intermediate spaces between the individual receivers and the smallest annular transmitter and between the adjacent annular transmitters are advantageously coated with sound-damping materials.

The present invention will be explained more fully with reference to an embodiment example shown in the accompanying drawings:

DESCRIPTION OF THE PREFERRED EMBODIMENTS

Figure 1:
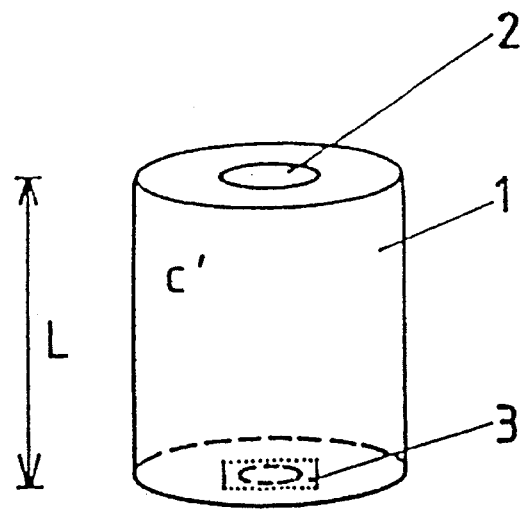
FIG. 1 shows an arrangement of the liquid-filled body according to the invention.
Figure 3:
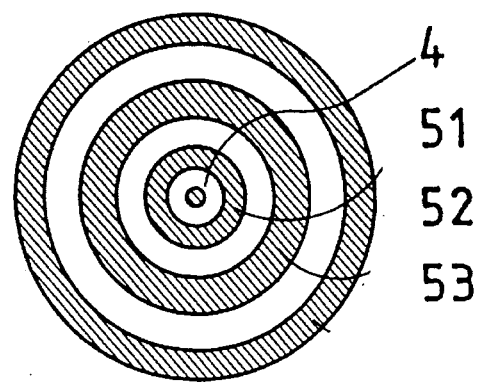
FIG. 3 shows a base plate according to the invention.

The essential component parts shown in FIG. 1 are the hollow cylinder 1 filled with liquid, its cover 2 and the base plate 3. The distance between cover 2 and base plate 3 equals length L. As can be seen from FIG. 3, the individual receiver 4 which extends over the smallest possible surface area is located in the center of base plate 3. The annular transmitters 51, 52, 53 are arranged around the individual receiver 4. The intermediate spaces between the individual transmitters 51, 52, 53 and between individual receiver 4 and transmitter 51 can advisably contain sound-damping substances.

The transmitters 51, 52, 53 and individual receivers 4 are acoustically coupled to the liquid via an impedance-matching layer system for the purpose of matching the ultrasonic impedances of the transmitter and receiver materials and the liquid. The liquid is selected in such a way that the ultrasonic speed equals $c'$.

Figure 2:
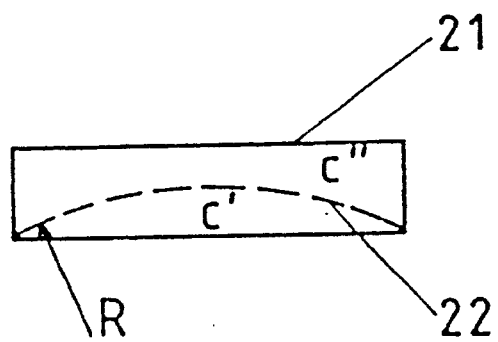
FIG. 2 shows a cover according to the invention.

The cover 2 according to FIG. 2 is made from a material with ultrasonic speed $c''$. The cover 2 has a plane outer side 21 serving as a supporting surface for the fingerprint. The inner side 22 of the cover 2 is concave with spherical radius R, where $c'$ is less than $c''$. Accordingly, the cover 2 acts as an ultrasonic lens with positive refractive power. The two sides of the cover 2 can advisably be provided with layers for impedance matching. The outer side 21 should be adapted to the ultrasonic impedance of water.

The ultrasonic waves emitted by the transmitters 51, 52, 53 penetrate the liquid and the ultrasonic lens formed by the cover 2 and arrive on the fingerprint to be analyzed. The ultrasonic waves are reflected and diffracted or scattered back at the different boundary layers of the skin structure and penetrate the ultrasonic lens and the liquid a second time in the opposite radiating direction.

By suitably selecting the parameters of $c'$, $c''$, L and R so as to satisfy the condition $$L=R/|(c''/c')-1|,$$

1:1 imaging of the ultrasonic transmitters on themselves is effected by means of the reflected ultrasonic waves. On the other hand, the reflected diffracted or backscattered ultrasonic waves arrive partially on the individual receiver 4 where they are converted into an electric signal. The amplitude of the receiver signal is proportional to the integral over an annular integrating region of the Fourier transforms of the fingerprint. Due to the rotational symmetry of the integrating region, this integral is invariant with respect to a rotation of the fingerprint on the outer side 21. The shape of the integrating area is determined by the shape of the active transmitter.

The phase of the electrical receiver signal oscillating at the frequency of the ultrasonic radiation depends upon the phase position of the spatial frequency of the fingerprint represented by the receiver signal and accordingly upon translational movements of the fingerprint on the outer side 21.

In order to overcome this dependency, the receiver signal must be converted in such a way that the frequency and phase information is eliminated. This is effected by the evaluating electronics, not shown, which contain means which rectify the alternating electric signal and are integrated (determination of effective value) via a fixed quantity of oscillation periods (quantity $\gg 1$).

In operation of the arrangement, the annular transmitters 51, 52, 53 can be operated individually and successively with respect to time as well as at the same time in different combinations.

It may also be advisable, in order to increase reliability of identification, to segment one or more annular transmitters and to actuate the individual annular segments successively in time.

In so doing, the pulse lengths of the respective radiated ultrasonic wave trains must be selected in such a way that the transmitters 51, 52, 53 are already inactive again when the sonic pulses strike the individual receiver 4 and the direct crosstalk from the transmitters 51, 52, 53 to the individual receiver 4 has already been damped via the sound-damping intermediate spaces.

In a second embodiment form, not shown in the drawing, the inner side 22 is convex, where $c'$ is greater than $c''$, rather than concave according to FIG. 2, where $c'$ is less than $c''$.

While the foregoing description and drawings represent the preferred embodiments of the present invention, it will be obvious to those skilled in the art that various changes and modifications may be made therein without departing from the true spirit and scope of the present invention.

What is claimed is:

1. A device for identifying fingerprints by use of ultrasound comprising:

a hollow cylinder, said cylinder being closed at ends thereof by a cover and a base plate having a center and being filled by a fluid, said cover being provided centrally thereof with a supporting surface for a finger to be identified;

an ultrasonic transmitter and an ultrasonic receiver being provided on the base plate; said ultrasonic receiver being arranged as an individual receiver in the center of said base plate; said ultrasonic transmitter being formed by at least one annular transmitter being arranged concentrically around said individual receiver;

an ultrasonic lens being arranged in said cover below said supporting surface so that ultrasound emitted by said ultrasonic transmitter and reflected at said supporting surface is imaged by said ultrasonic lens upon the ultrasonic transmitter; and evaluating means responsive to a signal generated by said ultrasonic receiver based on sonic pressure of received ultrasound for evaluating the fingerprint of the finger to be identified.

2. The device according to claim 1, wherein said ultrasonic lens includes a partially spherical surface which is constructed in said cover below the supporting surface at an inner side thereof, said partially spherical surface having a radius $$R = L|(c''/c') - 1|,$$

where L represents the distance between the base plate and the cover, c" represents the ultrasonic velocity between the supporting surface and the inner side, and c' represents the ultrasonic velocity in the liquid, said ultrasonic lens being constructed so as to be convex when c'>c" and concave when c'<41 .

3. The device according to claim 1, wherein said signal generated by said ultrasonic receiver is an alternating voltage signal and wherein said evaluating means rectifies said alternating-voltage signal and wherein said device also includes means for integrating the rectified alternating-voltage signal for a fixed number of periods.

4. The device according to claim 1, wherein said annular transmitter is divided into individual circle segments.

5. The device according to claim 1, wherein an intermediate space which is coated with sound-damping materials is provided between the individual receiver and said at least one annular transmitter.

6. The device according to claim 1, wherein a plurality of annular transmitters are provided and an intermediate space which is coated with sound-damping materials is provided between the individual receiver and the smallest annular transmitter of said plurality of annular transmitters.

7. The device according to claim 1, wherein a plurality of annular transmitters is provided and wherein every intermediate space between said annular transmitters is coated with sound-damping materials.

\* \* \* \* \*

UNITED STATES PATENT AND TRADEMARK OFFICE
CERTIFICATE OF CORRECTION

PATENT NO. : 5,563,345
DATED : October 8, 1996
INVENTOR(S) : Ralf T. Kersten et al It is certified that error appears in the above-indentified patent and that said Letters Patent is hereby corrected as shown below:

Claim 2, column 5, line 7, change "c'<41" to --c'<c"--.

Signed and Sealed this

Seventh Day of January, 1997

Attest:

BRUCE LEHMAN

Attesting Officer

Commissioner of Patents and Trademarks